United States Patent [19]

Zilberstein

[11] Patent Number: 5,188,594
[45] Date of Patent: Feb. 23, 1993

[54] METHOD OF ADMINISTERING MEDICATION INTO EPIDURAL SPACE

[76] Inventor: Michael Zilberstein, 3 trescott Path, Fort Salonga, N.Y. 11768

[21] Appl. No.: 733,675

[22] Filed: Jul. 22, 1991

[51] Int. Cl.$^5$ .............................................. A61M 31/00
[52] U.S. Cl. ........................................ 604/51; 128/748
[58] Field of Search .................. 604/49, 51, 117, 118, 604/121, 246, 248, 32; 128/747, 748

[56] References Cited

U.S. PATENT DOCUMENTS

| | | | |
|---|---|---|---|
| 3,185,179 | 5/1965 | Harautuneian | 604/248 |
| 3,434,691 | 3/1969 | Hamilton | 604/248 |
| 3,468,308 | 10/1969 | Bierman | 604/118 |
| 4,164,938 | 8/1979 | Patton | 128/748 |
| 4,215,699 | 8/1980 | Patel | 128/748 |
| 4,623,335 | 11/1986 | Jackson | 604/118 |
| 4,799,494 | 1/1989 | Wang | 604/51 |
| 4,801,293 | 1/1989 | Jackson | 604/117 |
| 4,944,724 | 7/1990 | Goldberg et al. | 604/118 |

FOREIGN PATENT DOCUMENTS

| | | | |
|---|---|---|---|
| 0032826 | 7/1981 | European Pat. Off. | 604/121 |
| 0091846 | 10/1983 | European Pat. Off. | 604/118 |

Primary Examiner—John D. Yasko
Assistant Examiner—Anthony Gutowski
Attorney, Agent, or Firm—Ilya Zborovsky

[57] ABSTRACT

A method of administering medicine into the epidural space by first supplying air through a valve connected to a needle and provided with an inflatable element so that before the needle reaches the epidural space the inflatable element is inflated. The needle is advanced and when the needle reaches the epidural space the inflatable element is deflated; medication is then administered through the valve and through the needle into the epidural space.

2 Claims, 3 Drawing Sheets

STAGE 2

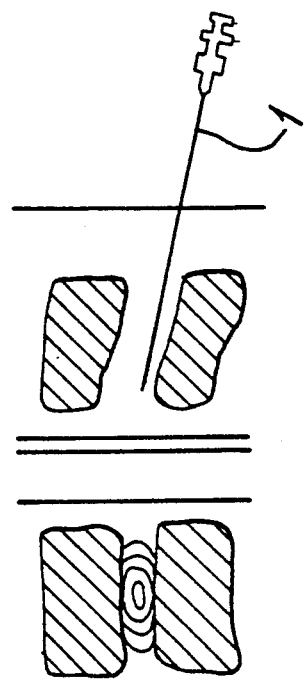
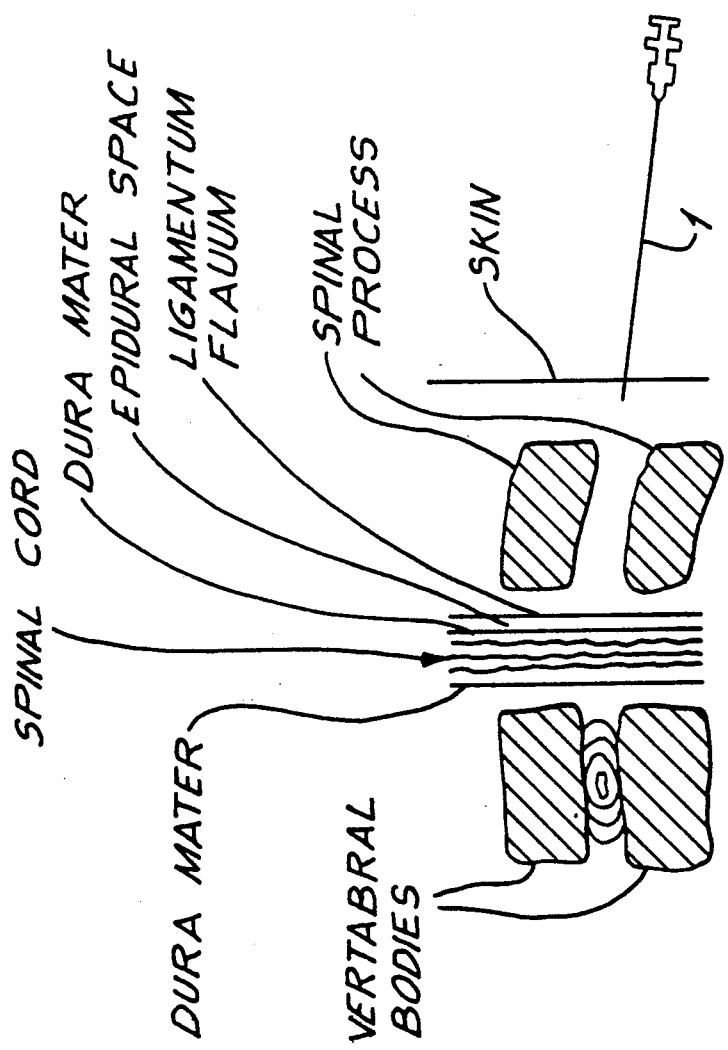
FIG. 2
STAGE 1
FIG. 1
STAGE 1

STAGE 2

STAGE 2

STAGE 3

STAGE 3

POSITION 1

POSITION 2

POSITION 3

POSITION 4

METHOD OF ADMINISTERING MEDICATION INTO EPIDURAL SPACE

BACKGROUND OF THE INVENTION

The present invention relates to a device for and a method of administering a medication into epidural space.

During the last decade the regional block analgesia (spinal and epidural) achieved widespread popularity among anesthesiologists. The region block provided excellent analgesia and muscle relaxation during surgical procedure. In addition it is also beneficial to the patients in postoperative period, as well as to some patients suffering from pain of different etiology. It is generally accepted that epidural block has many advantages compared to the spinal: absence of headaches and relatively gradual and delayed hypotension are just some of them. The main problem with epidural block is the difficulty of accurate identification of the epidural space, which may explain occasional failure of this type of analgesia. To identify the epidural space most anesthesiologists use the so-called method of loss of resistance to injection. The method based on the fact that the piston of the syringe, filled with air or fluid, meets resistance and bounces during the injection attempt, when the bevel of the needle is located in the rigid tissues superficial to the epidural space, especially ligamentum flavum. When the bevel of the needle reaches the epidural space, the piston of the syringe has to move easily due to the loss of the resistance to injection. In the practice it is not always so obvious due to some drawbacks of the described method.

The above described method has the following drawbacks:

1. The method is not completely objective. Using this method the practitioner in a great degree relies on his own experience and his individual ability to sense changes in pressure. Both these qualities are rather subjective. Therefore, in not very clear cases of loss of resistance, practitioners may have different opinions regarding correct placement of the epidural needle.

2. The movement of the piston along side the walls of a syringe by itself meets some resistance, especially significant, if during the advance of the epidural needle some blood enters the syringe. In these instances it is very difficult to recognize the loss of resistance. As a result the epidural needle may be placed in the subarachnoid space with all of the undesirable consequences: severe headaches in postoperative period or if the misplacement of the needle is not recognized immediately and the local anesthetic administered, total spinal block—a very dangerous life-threatening complication.

3. This method requires use of a needle of a big diameter. As a matter of fact all epidural sets available contain only #17 or less often #18 gauge needles. Introduction of these needles may not be very pleasant to the patients.

SUMMARY OF THE INVENTION

Accordingly, it is an object of the present invention to provide a device for and a method of administering a medication into an epidural space, which avoids the disadvantages of the prior art.

In keeping with these objects and with others which will become apparent hereinafter, one feature of the present invention resides, briefly stated, in a device for administering medication into epidural space, which has a hollow needle having front and rear ends, a value connectable with said rear end with the rear end of the needle and having a first opening arranged to open into the needle, a second opening closeable by an elastic member and a third opening, an air supplying element adapted to be connected with the third opening so that when the needle is inserted into a chosen area air is supplied by the air supplying element through the value into the needle and then out of its front end and before entering the epidural space the elastic member is inflated while after entering the epidural space the elastic member is deflected, and a medication administering element connectable with the third opening of the valve when the air supplying element is removed from the third opening so that the medication administering element fits the medication through the valve and then through the needle into the epidural space when the elastic member is deflected.

When the device is designed and the method is performed in accordance with the present invention the amount of epidural block failures is decreases and in some cases the complications relating to inadvertent subarachnoid needle placement is prevented. The method and device allows the use of needles which are smaller in diameter, so that the patient feels much more comfortable such as for example when 25 gauge Whitacer spinal needle for epidural analgesia has been used. The idea to use the rubber balloon method belongs to Macintosh R. R. 1950. However, the method never became popular and nowadays it is completely abandoned mostly because the original technique proposed by the author is inconvenient for practical use, cumbersome and time consuming.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 1-6 are views showing successive stages of administering a medication into epidural space.

DESCRIPTION OF THE PREFERRED EMBODIMENTS

Figure 3:
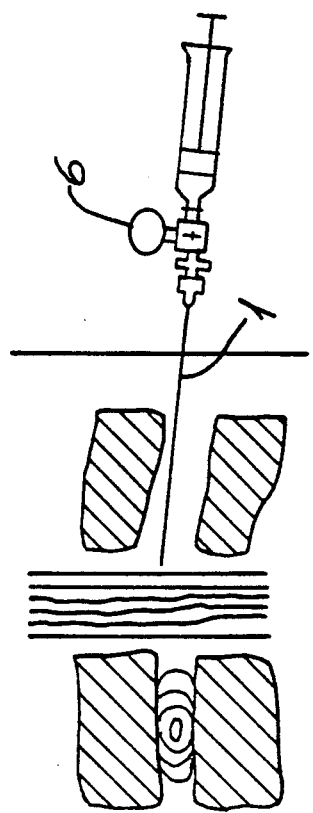

A device for administering a medication into epidural space has a conventional hollow needle which is identified as a whole with reference numeral 1 and includes front and rear ends. The device further has a valve 2 which is provided with a passage including three openings 3, 4 and 5. An elastic member 6 is adapted to be fitted onto opening 4, for example on a flange 4' provided in the region of the opening 4. The opening 3 and 5 have a male formation 3' and a female formation 5'. The valve has a valve member 7 which is turnable between several positions as will be explained hereinbelow. The device further has an air supplying element 8 formed for example as a syringe with a piston and a piston rod.

Figure 4:
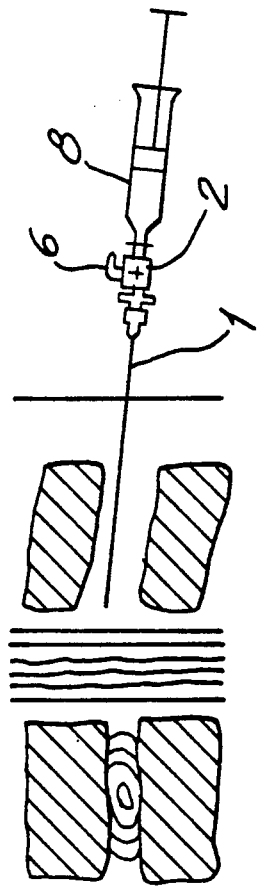
Figure 5:
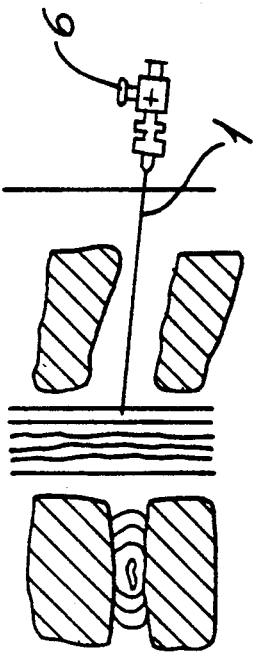

The device operates and the method is performed in the following manner:

First as shown in FIGS. 1 and 2 illustrating stage one, the epidural needle 1 with an intruder inside is inserted into a chosen area until it reaches the space between the spinal processes. At this point the intruder is removed as shown in FIGS. 3 and 4 illustrating stage two.

Figure 7:
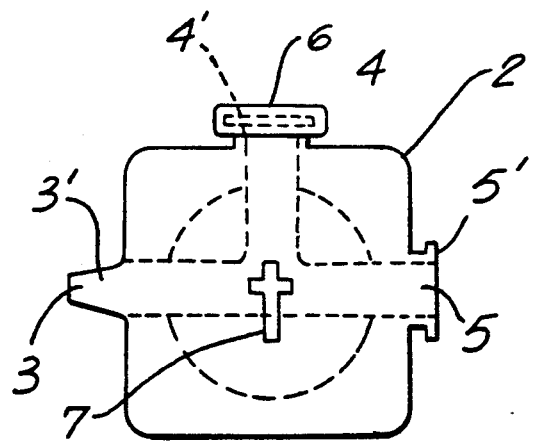
FIGS. 7-10 are views showing positions of a valve of the inventive device.

Then the three-way valve 2 is inserted with its female formation 3 into the rear end of the needle 1. The syringe filled with air is inserted into the female formation 5 of the valve. The valve is turned by a not shown handle extending from the valve member 3 outside of the valve so that as shown in FIG. 7 all three passages 3, 4, 5 are open. Then the air is injected by the displacement of the piston in the syringe 8. If the injection of air does not cause inflation of the elastic member 6 which can be formed as a rubber balloon, the needle 1 has to be advanced further until a stable, without any leak, rubber balloon is created as shown in FIG. 4. This means that a bevel of the needle 1 is inserted into ligamentum flavum.

Figure 6:
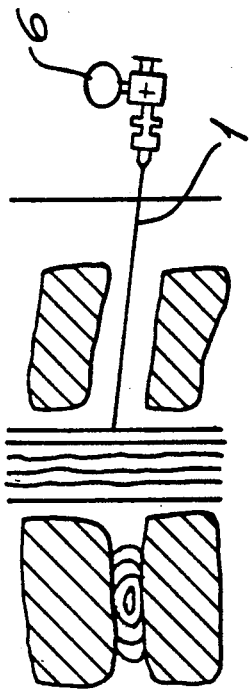
Figure 8:
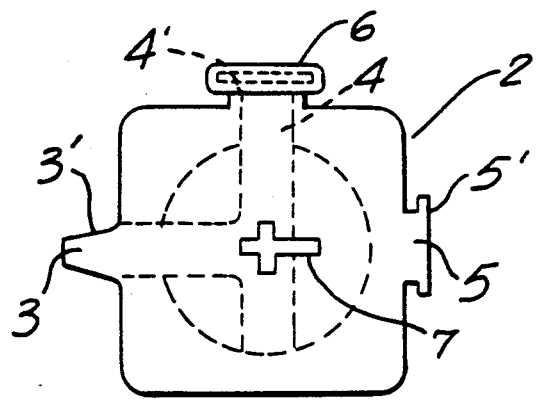
Figure 9:
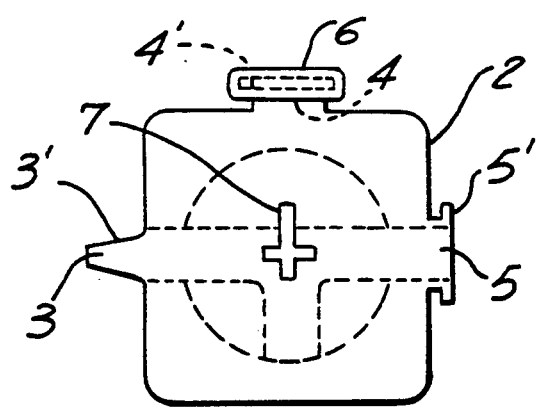
Figure 10:
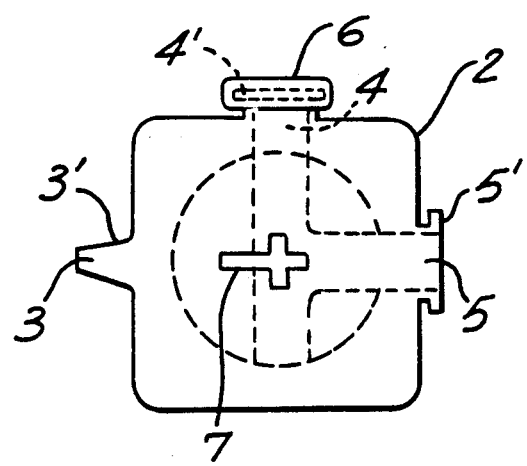

In the stage three with the rubber balloon inflated, the valve member is turned to the position 2 shown in FIG. 8 to close the opening 5 and the syringe 8 is disconnected. Then the needle is slowly advanced further until the balloon collapses as shown in FIG. 6. This means that the bevel of the needle 1 reaches the epidural space. Then a chosen medication is administered into the epidural space by inserting an administering element, for example a syringe with medication, into the opening 5 of the valve 2. Of course, the valve member 7 is turned so as to provide a communication between the opening 5 and the opening 3 (as shown in FIG. 9). In accordance with the preferred embodiment, during this process the opening 4 is closed so as to prevent any spilling of the medication through it.

When the device is designed and the method is performed in accordance with the present invention the following advantages are provided:

1. The method is objective: The inflation of stable rubber balloon, which proves that the needle is in ligamentum flavum is obvious to anybody regardless of the experience and the individual ability to sense changes in the resistance. The same could be said about the collapse of the balloon, which occurs when the bevel of the needle reaches the epidural space.

2. Presence of blood in the needle, which is difficult to avoid during regional block does not influence the accuracy of epidural space identification.

3. This method allows the use of needles smaller than usual in diameter, which makes the epidural placement of the needle less painful to the patient.

The invention is not limited to the details shown, since various modifications and structural changes are possible without departing in any way from the spirit of the present invention.

What desired to be protected by Letters Patent is set forth in particular in the appended claims.

I claim:

1. A method of administering medication into an epidural space, comprising the steps of introducing a front end of a hollow needle into a chosen space; connecting a rear end of the hollow needle with a valve having a first opening connectable with the rear end of the needle, a second opening and a third opening; attaching an elastic member to said second opening of said valve; supplying air by an air supplying element into said third opening and then through the first and second openings and advancing the needle so that when the needle does not reach the epidural space the elastic element is inflated and forms a balloon and when the needle reaches the epidural space the balloon is deflected due to the communication of said valve with the epidural space; removing the air supplying element from the third opening of the valve when the balloon is deflected; connecting a medicine administering element to the third end of the valve, and supplying a medicine through the third end and the first end of the valve into the needle and then into the epidural space.

2. A method as defined in claim 1; and further comprising the step of closing by the valve member the second opening during supplying of the medicine.

* * * * *